United States Patent
Leiteritz et al.

(10) Patent No.: US 7,899,947 B2
(45) Date of Patent: Mar. 1, 2011

(54) METHOD FOR SETTING UP DATA LINK BETWEEN MEDICAL APPLIANCES AND COMPUTER SYSTEM

(75) Inventors: Stefan Leiteritz, Vienna (AT); Joerg Schmitt, Osburg (DE)

(73) Assignee: Agfa HealthCare NV, Mortsel (BE)

( * ) Notice: Subject to any disclaimer, the term of this patent is extended or adjusted under 35 U.S.C. 154(b) by 134 days.

(21) Appl. No.: 12/356,693

(22) Filed: Jan. 21, 2009

(65) Prior Publication Data

US 2009/0164669 A1 Jun. 25, 2009

Related U.S. Application Data

(63) Continuation of application No. PCT/EP2007/056899, filed on Jul. 6, 2007.

(30) Foreign Application Priority Data

Jul. 24, 2006 (EP) .................................. 06117734

(51) Int. Cl.
*G06F 3/00* (2006.01)
*G06F 13/12* (2006.01)
*G06F 7/04* (2006.01)
(52) U.S. Cl. ................................. 710/11; 710/62; 726/2
(58) Field of Classification Search ........................ None
See application file for complete search history.

(56) References Cited

U.S. PATENT DOCUMENTS

| | | | |
|---|---|---|---|
| 6,275,869 B1 * | 8/2001 | Sieffert et al. ................ | 719/321 |
| 2006/0041917 A1 | 2/2006 | Vellanki et al. | |
| 2006/0136594 A1 | 6/2006 | Tung | |

OTHER PUBLICATIONS

International Search Report dated Feb. 13, 2008, from corresponding International application PCT/EP2007/056899 filed Jul. 6, 2007.

Translation of the International Preliminary Report on Patentability dated Feb. 17, 2009 from counterpart International Application No. PCT/EP2007/056899, filed Jul. 6, 2007.

* cited by examiner

*Primary Examiner*—Alan Chen
(74) *Attorney, Agent, or Firm*—Houston Eliseeva LLP

(57) ABSTRACT

A method and system of setting up a data link between medical appliances (M1-M6) and a computer system (1) in which for each of the medical appliances (M1-M6) at least one communication protocol (P1-P6) is stored together with the communication parameters (K1a, K1b, K1c ... -K6a, K6b, K6c ...) assigned to this communication protocol (P1-P6). The method comprises the following steps: setting communication parameters (K1a, K1b, K1c ... -K6a, K6b, K6c ...) of a communication protocol (P1-P6); receiving data from a medical appliance (M1-M6); checking whether the data received from the medical appliance (M1-M6) correspond to sample data which are characteristic for the communication protocol (P1-P6); repetition of steps a. to c. with other communication parameters (K1a, K1b, K1c ... -K6a, K6b, K6c ...) of the communication protocol (P1-P6) if the data received from the medical appliance (M1-M6) do not correspond to the sample data and setting up a data link between the medical appliance (M1-M6) and the computer system (1) using the communication protocol (P1-P6) if the data received from the medical appliance (M1-M6) correspond to the sample data. In this way a reliable data link is automatically produced between the medical appliances (M1-M6) and the computer system (1).

22 Claims, 4 Drawing Sheets

METHOD FOR SETTING UP DATA LINK BETWEEN MEDICAL APPLIANCES AND COMPUTER SYSTEM

RELATED APPLICATIONS

This application is a Continuation of PCT application number PCT/EP2007/056899, filed on Jul. 6, 2007 which claims priority to European Patent Application No. EP06117734.1 filed on Jul. 24, 2006, both of which are incorporated herein by reference in their entirety.

BACKGROUND OF THE INVENTION

In hospitals software systems are used for the documentation of patient-related information. This information includes among other things measurements from medical appliances which monitor and/or affect the state of the patient. In general the medical appliances have interfaces in order to make data, such as e.g. measured or set values and alarm data, electronically available.

Patient documentation systems make use of different software modules in order to receive and further process the data from the medical appliances, for example displaying and/or storing said data. For this purpose the medical appliances are connected to computers so-called interface PCs—which take on the function of an interface between the individual medical appliances on the one hand and the systems processing the data on the other hand.

There are a large number of different medical appliances with different communication protocols which require different interface settings. These are for example patient monitoring, breathing or anesthesia appliances such as e.g. IntelliVue MP90 made by Philips Medical Systems, Solar 8000 made by GE Healthcare, Infinity Delta made by Dräger/Siemens, AS/3 made by Datex, Evita2 made by Dräger, Servo 300 made by Maquet, Zeus made by Dräger and Aestiva/5 made by Datex.

The connection of a new medical appliance to an interface PC or changing one medical appliance for another medical appliance is generally associated with a series of settings both on the medical appliance and on the interface PC which must generally be made by the medical staff.

First of all the driver software belonging to a medical appliance must be chosen. However, this is not always immediately available or known for the respective medical appliance. Moreover, a medical appliance can allow a number of different communication parameters. The communication parameters include e.g. the data transmission rate (baud rate), the number of data bits, the parity, the number of start and stop bits and the type of flow control used. Also, the permissible communication parameters are not always known, and so the latter must first of all be read off from the medical appliance. For this, if applicable systems menus must be opened which can be protected by requiring a password. Therefore, the inputting of the communication parameters is often found by the staff members involved to be tiresome, or is even forgotten, and moreover it is prone to error.

If the aforementioned settings are not made or are made erroneously, no data link to the medical appliance can be established, and so data, such as e.g. values measured with the measuring appliance or set on the measuring appliance, are lost.

SUMMARY OF THE INVENTION

The application relates to a method of setting up a data link between medical appliances and a computer system.

It is the object of the invention to specify a method of setting up the most reliable possible data link between medical appliances and a computer system.

In general according to one aspect, the invention features a method of setting up a data link between medical appliances and a computer system in which for each of the medical appliances at least one communication protocol is stored together with the communication parameters assigned to this communication protocol The method includes:

a. setting communication parameters of a communication protocol;

b. receiving data from a medical appliance;

c. checking whether the data received from the medical appliance correspond to sample data which are characteristic for the communication protocol;

d. repetition of steps a. to c. with other communication parameters of the communication protocol if the data received from the medical appliance do not correspond to the sample data;

e. setting up a data link between the medical appliance and the computer system using the communication protocol if the data received from the medical appliance correspond to the sample data.

In general, according to another aspect, the invention features, a computer system that sets up a data link to medical appliances in which for each of the medical appliances at least one communication protocol is stored together with the communication parameters assigned to this communication protocol, wherein the computer system:

a. sets communication parameters of a communication protocol;

b. receives data from a medical appliance;

c. checks whether the data received from the medical appliance correspond to sample data which are characteristic for the communication protocol;

d. repeats of steps a. to c. with other communication parameters of the communication protocol if the data received from the medical appliance do not correspond to the sample data;

e. sets up a data link between the medical appliance and the computer system using the communication protocol if the data received from the medical appliance correspond to the sample data.

In the case where the medical appliance only sends data to the computer system upon a request, the sending of a request to the medical appliance can be provided between steps a. and b.

A communication protocol is a specification of the form in which data are exchanged between the medical appliances and the computer system. This specification comprises a set of rules and formats (syntax).

The communication parameters of a communication protocol are to be understood as being those parameters the values of which must be set before establishing a data link between the respective medical appliance and the computer system. These include for example:

the data transmission rate (baud rate) which specifies the speed of the data transmission in the unit bits/second, the number of data bits in a data word, the parity which is used for error detection, the number of stop bits for detection of the data word end, the number of start bits for detection of the data word start, and the flow control (none, software or hardware).

The respective values of the communication parameters are set on the medical appliance and must be set to the same values in order to set up the data link in the software of the computer system—of the so-called interface software.

The sample data respectively to be expected with a communication protocol can be established by analyzing the response data to be expected of the medical appliance according to the manufacturer's specifications, e.g. in the form of descriptions of the medical appliances. By establishing both unchanging and variable sections in the response data to be expected, a sample can be derived which is then used for the analysis. If e.g. the data is transmitted from the appliance, one can easily establish the position of the latter in the response and at the same time its structure (e.g. "2006-01-31" or "31.01.2006"). This information can also be used to generate the sample data. Regular expressions are preferably used here. Regular expressions (abbreviated as "RegExp" or "Regex") are used to describe (sub-)quantities of character strings with the aid of syntactic rules.

The solution according to the invention is based upon the idea of establishing a data link automatically, i.e. without any additional actions by a user, between the computer system—in particular the so-called interface PC—and the individual medical appliances connected to the latter. Here the communication protocol used by the respective medical appliance, including the associated communication parameters, are automatically established by the computer system and are set upon setting up the data link. Detection of specifically which medical appliance one is dealing with (e.g. manufacturer's name and type denomination) is not required here.

By automatically establishing the appropriate communication protocol it is checked whether a medical apparatus connected to the corresponding serial interface of the interface PC "speaks" a specific communication protocol. If yes, the driver software module of the medical appliance corresponding to the communication protocol is activated in the computer system. The driver software is understood as meaning the technical software conversion of the communication protocol. The driver software communicates with the appliance, establishes or breaks off the data link, requests current measurement data, etc.

If, however, no appropriate response is received, either no medical appliance is linked to the interface PC or the respective medical appliance does not "speak" this protocol, but rather a different protocol, or the communication parameters do not correspond to those of the medical appliance. In this case, according to the invention the communication parameters assigned to the communication protocol are changed and detection is attempted once again.

If after this no response or a false response is received once again, the next software module is activated which tries to set up a data link with the medical appliance using a different communication protocol in the way described above.

This process is repeated with all possible software modules and communication protocols until a data link with the medical appliance can be produced.

Preferably, the process described above is also followed if no medical appliance is linked to the interface PC. If with this embodiment of the invention a medical appliance is connected to the interface PC, a data link is automatically produced without the process needing to be initiated by a user action.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
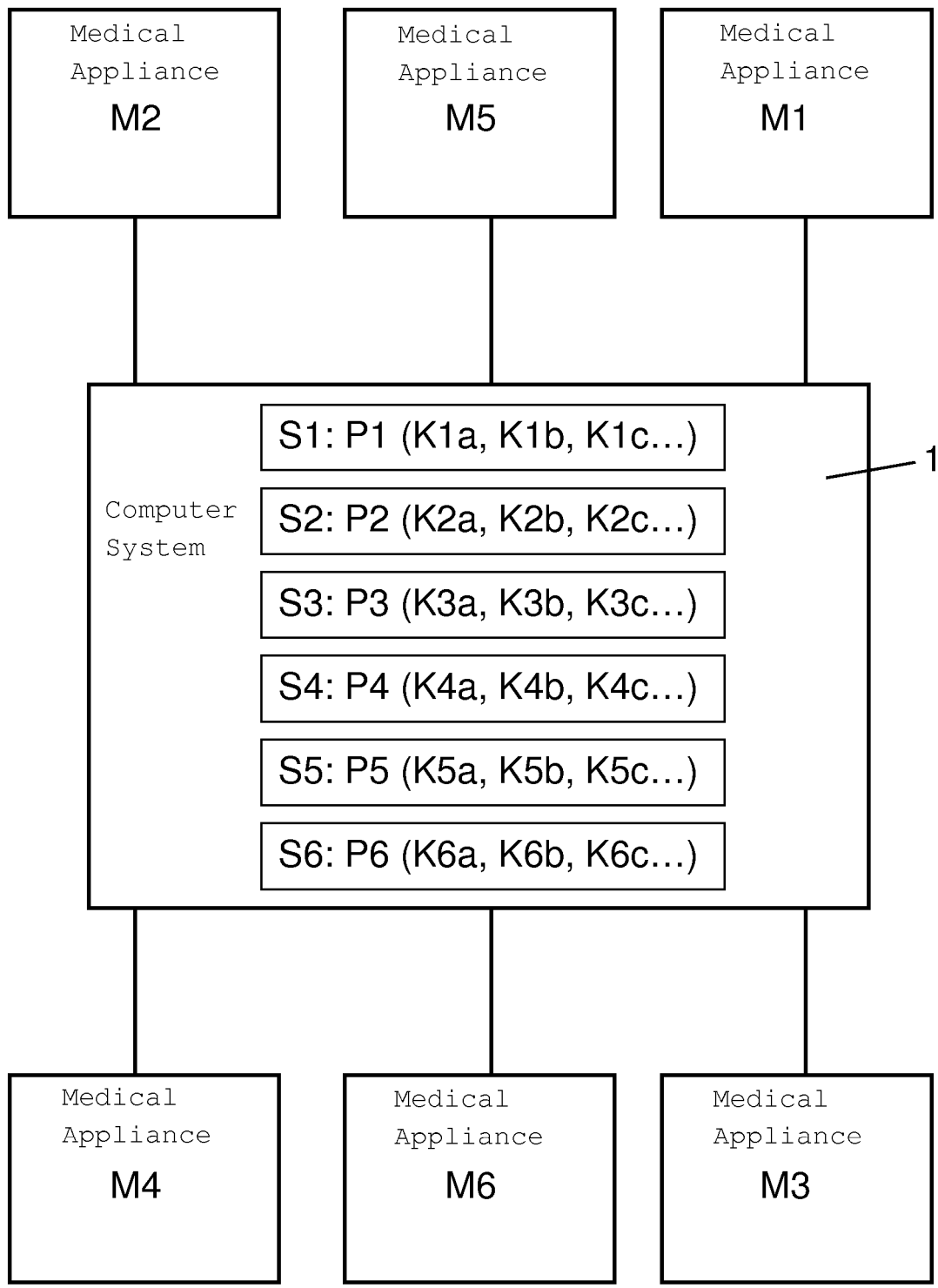
FIG. 1 is a block diagram showing a computer system for implementing the method according to the invention.

FIG. 1 shows a computer system 1 for implementing the method according to the invention. Individual medical appliances M1 to M6 are linked to the computer system 1 by electric wires and/or wirelessly, e.g. by infrared or radio frequency radiation.

For each of the medical appliances M1 to M6 there is at least one communication protocol P1 to P6 to which a number of communication parameters K1$a$, K1$b$, K1$c$ . . . to K6$a$, K6$b$, K6$c$ . . . are respectively assigned.

The definition of the individual communication protocols P1 to P6 including the respectively assigned communication parameters K1$a$, K1$b$, K1$c$ . . . to K6$a$, K6$b$, K6$c$ . . . is generally taken from the details provided by the respective medical appliance manufacturer and stored in the computer system 1.

As examples, in the following the communication protocols P1 and P2 required for communication with the medical appliances M1 and M2 and the respectively permissible values of the communication parameters are specified:

| Medical appliance | M1 | M2 |
|---|---|---|
| Communication protocol | P1 | P2 |
| Appliance type | Breathing appliance | Anesthesia appliance |
| Baud rates | <u>2400</u>, 4800, 9600 | <u>1200</u>, 4800, 19200 |
| Data bits | 7, <u>8</u> | 7, <u>8</u> |
| Start bits | <u>1</u> | <u>1</u> |
| Stop bits | <u>1</u> or 2 | <u>1</u> |
| Parity | <u>even</u> or odd | <u>Even</u> |

For each communication protocol P1 to P6 there is a software module S1 to S6 with the help of which the communication protocol P1 to P6 respectively required for communication with the individual medical appliances can be automatically detected. Software modules S1 to S6 are loaded into the computer system 1 before starting the process and are kept in a list, such as database, here—as indicated in FIG. 1. Next the individual software modules S1 to S6 are activated in sequence.

First of all the first software module S1 in the list is activated. The latter attempts to establish a data link to a first medical appliance, e.g. M2, of the connected medical appliances M1 to M6 using the first communication protocol P1 according to the method according to the invention.

If no data link can be produced here between the first medical appliance M2 and the computer system 1, the next second software module S2 found in the list is started. The latter then attempts to establish a data link to the first medical appliance M2 using the second communication protocol P2. If this attempt is also without success, the further software modules S3 to S6 in the list are activated in sequence until a data link with the first medical appliance M2 is produced.

The method described is correspondingly repeated for the other medical appliances M1, M3 to M6.

With the method according to the invention of setting up a data link by using a communication protocol, e.g. P1, by means of the corresponding software module S1 the values of the individual communication parameters K1*a*, K1*b*, K1*c* ... are first of all set, such as e.g. the data transmission rate, the number of data bits per data word, the parity and the number of start and stop bits. Preferably the communication parameters are set to values here which—e.g. according to the manufacturer's specifications or according to experience—are used most frequently with this communication protocol. In the table shown above with communication protocols P1 and P2, these values are underlined. In the present example of the first communication protocol P1, these values are as follows: data transmission rate 2400 bit/s, 8 data bits, number of start and stop bits respectively 1, parity even.

There are two different types of communication protocol. With a first type a request must be sent to the medical appliance before the medical appliance sends data back as a response. With a second type the medical appliance sends data independently.

If data are now received from the first medical appliance M2—depending on the type of communication protocol if appropriate only after sending a request—, these data are compared with sample data which are characteristic for the first communication protocol P1 and distinguishes the latter unambiguously from the sample data of the other communication protocols P2 to P6.

If the data of the first medical appliance M2 correspond to the sample data, a data link between the first medical appliance M2 and the computer system 1 is produced using the first communication protocol P1. If this is not the case, the values of the communication parameters of the first communication protocol P1 are first of all changed and the aforementioned steps are implemented upon the basis of the changed communication parameters. In the specified example, the communication parameters are set to values which are used the second most frequently with the first communication protocol P1, such as e.g. data transmission rate 4800 bit/s, 7 data bits per data word, number of start bits 1 and stop bits 2, parity uneven.

When examining the data received from the first medical appliance M2, any possible communication errors, such as e.g. a so-called framing error or parity error, is moreover incorporated into the analysis and if appropriate the communication parameters are changed.

A framing error always occurs if the communication parameters do not correspond with both communication partners, e.g. with the following settings of the medical appliance:

7 data bits, 1 start bit, 1 stop bit, parity bit even and the following settings of the communication module on the interface PC:

8 data bits, 1 start bit, 1 stop bit, parity bit even.

This means that when sending a 7 bit data word from the medical appliance, a total of 10 bits are used and 11 bits are expected by the interface PC. The "framing" of this communication is therefore incorrect.

A parity error occurs if the transmission of data is interrupted. In order to detect this, the transmitter calculates a parity from the bits to be transmitted and transmits this to the receiver. The receiver firstly receives all of the bits, from these calculates the parity and compares it with that communicated by the transmitter. If the value of this parity bit differs, there is a transmission error. In the communication protocol used it is then mostly defined how such a case should be handled.

It is preferably also checked whether the communication protocol has been detected without any doubt and unambiguously. If the first response corresponds to the expected response, it can however still be the case that a different communication protocol would also have produced the appropriate response. In such a case, further requests are necessary until the communication protocol used is identified without any doubt.

The following example of two similar communication protocols should clarify this: With both communication protocols the communication is established by a corresponding command (initialize communication command). With the first protocol the command code 0x2D means the request for the current upper alarm limits. However, with the second protocol the same command means the request for the current monitor data. With the first protocol the command code 0x52 means the request for the appliance identification. In order to request the appliance identification in the second protocol however, the command code 0x2C is to be used.

It is clear from this that the comparison of the response to the ICC command alone is not sufficient in order to unambiguously identify the protocol, but that further requests and comparisons (e.g. the request for the appliance identification) are necessary.

Figure 2:
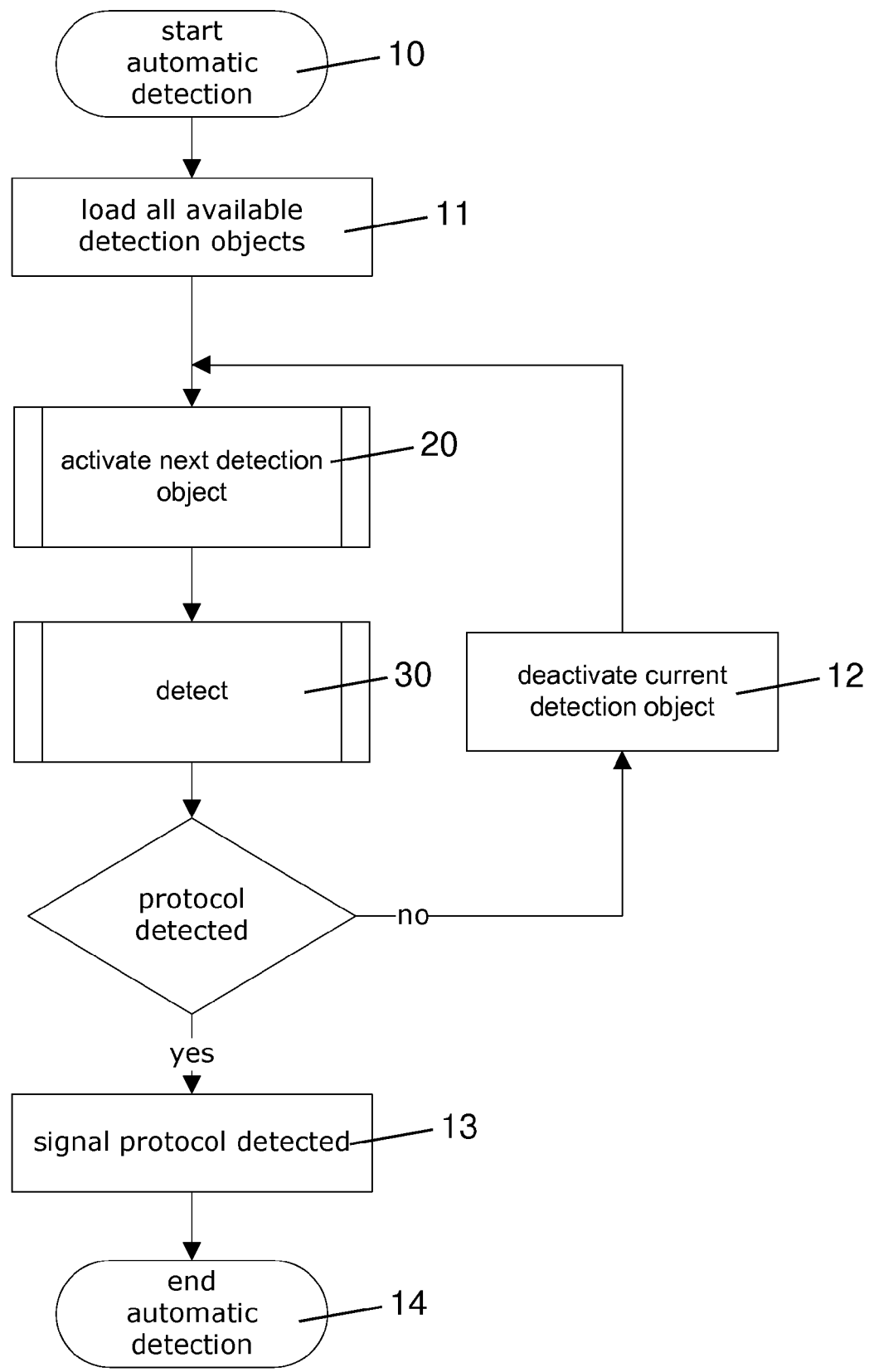
FIG. 2 is a flow chart of an example of the method according to the invention.

FIG. 2 shows a flow chart of an example of the method according to the invention for automatic appliance detection.

After the start 10 of the process all available software modules for detection of the different communication protocols (detection objects) are loaded 11 and arranged in a list.

In a further part process 20 of the method the first or respective next software module for detecting a communication protocol is started.

In the following part process 30 different steps are then taken for automatically detecting the communication protocol. If the communication protocol does not correspond to the required protocol of the medical appliance, the first software module is deactivated 12 and the part processes 20 and 30 for further software modules from the list for detecting the further communication protocols are repeated until the communication protocol appropriate to the respective medical appliance has been unambiguously identified 13. In this case a data link is produced between the medical appliance and the computer system using the communication protocol established, and the process for automatic appliance detection is ended 14.

Figure 3:
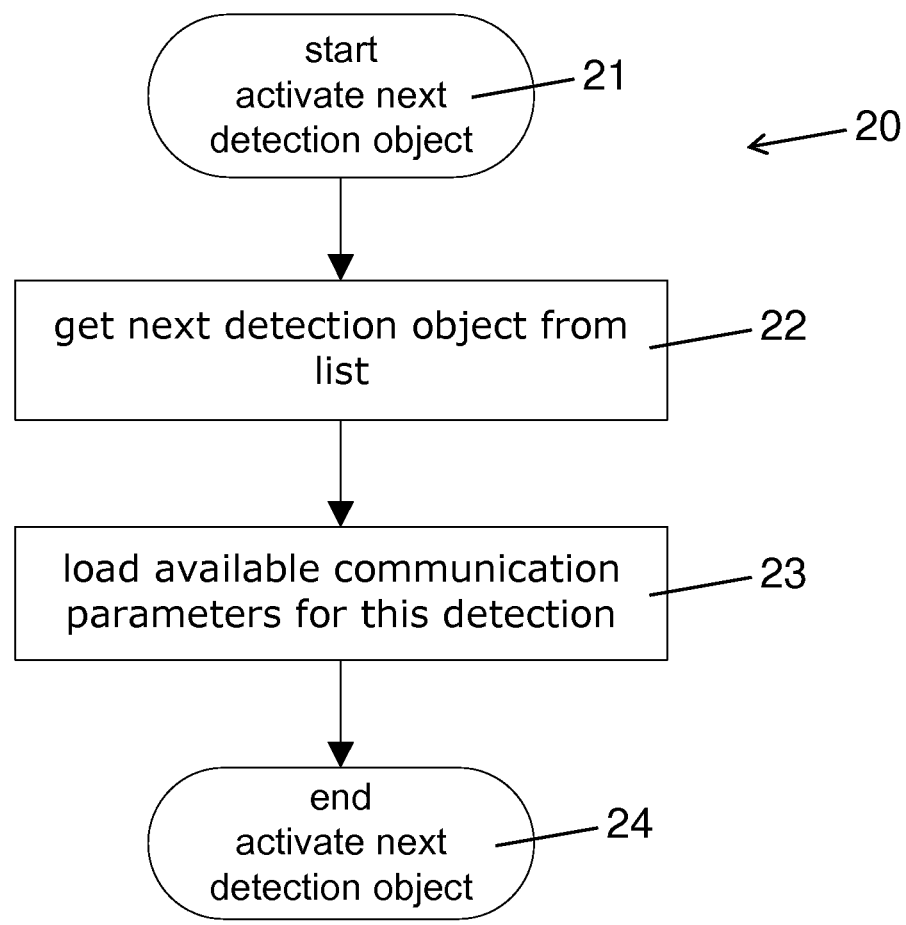
FIG. 3 is a flow chart of a part process of the method illustrated in FIG. 2.

FIG. 3 shows a flow chart of the part process 20 for starting the first software module or further software modules for detecting communication protocols.

After the start 21 of this part process 20 the software module given as the respective next one in the list is used 22. Next the communication parameters assigned to this communication protocol and the values of the latter—preferably those most likely to be used—are loaded or set 23. The part process 20 is then ended 24.

Figure 4:
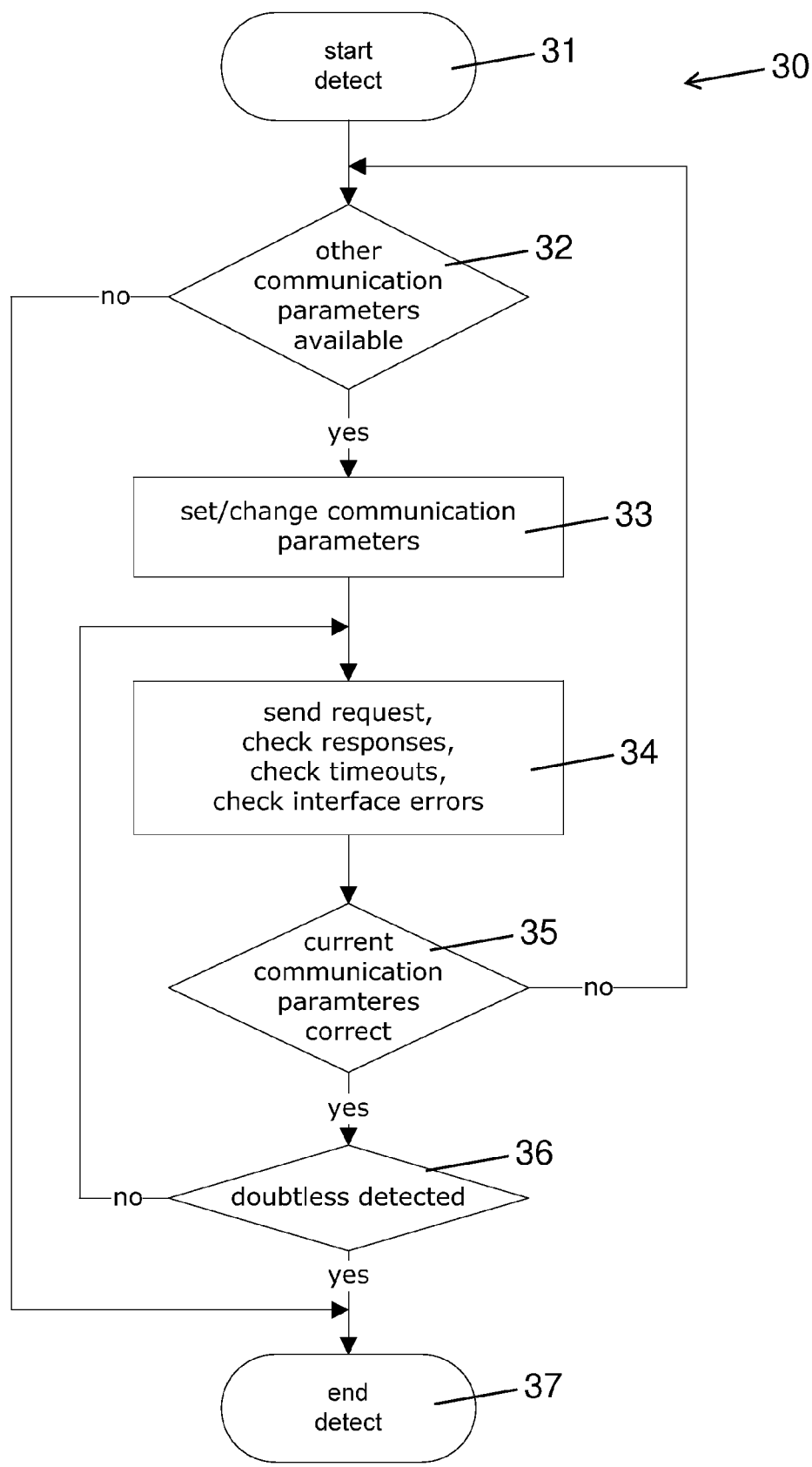
FIG. 4 is a flow chart of a further part process of the method illustrated in FIG. 2.

The part process 30 following on from part process 20 is illustrated in detail in FIG. 4.

After the start 31 it is first of all checked whether communication parameters or further communication parameters are available 32. If this is not the case, the part process 30 is ended 37. In the event that (further) communication parameters are available, these are set or changed 33. A request is then sent to the medical appliance and the answers received from the medical appliance examined. Depending on the type of communication protocol the sending of a request can, if appropriate, be dispensed with. If the following check 35 shows that the communication parameters do not correspond to those of the respective medical appliance, the aforementioned steps 32 to 34 are repeated for further communication parameters in so far as such parameters are available.

In the event that the communication parameters set correspond to those of the medical appliance, it is examined in a further process step 36 whether the respective communication protocol has been detected unambiguously and without any doubt. If this is not the case, steps 34 and 35 are repeated by further responses from the medical appliance being examined. If there is doubt-free detection of the respective communication protocol, the part process 30 can be ended 37.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of setting up a data link between medical appliances and a computer system in which for each of the medical appliances at least one communication protocol is stored together with the communication parameters assigned to this communication protocol, the method comprising:
   a. setting communication parameters of a communication protocol;
   b. receiving data from a medical appliance;
   c. checking whether the data received from the medical appliance corresponds to sample data which are characteristic for the communication protocol;
   d. repeating steps a. to c. with other communication parameters of the communication protocol if the data received from the medical appliance do not correspond to the sample data;
   e. setting up a data link between the medical appliance and the computer system using the communication protocol if the data received from the medical appliance correspond to the sample data.

2. The method according to claim 1, further comprising repeating steps a. to e with at least one further communication protocol if it was not possible to set up a data link between the medical appliance and the computer system.

3. The method according to claim 1, further comprising repeating steps a. to e. for at least one further medical appliance.

4. The method according to claim 1, further comprising assigning the communication parameters to a communication protocol occurring in this communication protocol with different likelihood and in step a. those communication parameters being set which have the highest likelihood.

5. The method according to claim 1, wherein the sample data characteristic for the respective communication protocol unambiguously differs from sample data of other communication protocols.

6. The method according to claim 1, wherein the sample data characteristic for a communication protocol is established by an analysis of response data from a medical appliance.

7. The method according to claim 1, before step b. a request is sent to the medical appliance and in step b. the data sent from the medical appliance upon the request made of the medical appliance being received.

8. The method according to claim 1, before setting up the data link in step e. the computer system examines whether the first communication protocol has been unambiguously identified.

9. The method according to claim 1, further comprising assigning and activating a software driver module in order to set up the data link in step e. to the medical appliance assigned to the communication protocol in the computer system.

10. A method for determining a communication protocol between a computer and a medical appliance prior to connecting the medical appliance to the computer, the method comprising:
   a. setting communication parameters of the communication protocol;
   b. deriving sample data by analyzing response data to be expected of the medical appliance according to manufacturer specifications;
   c. checking whether the derived sample data of the medical appliance corresponds to sample data which are characteristic for the communication protocol;
   d. repeating steps a. to c. with other communication parameters of the communication protocol if the derived sample from the medical appliance do not correspond to the sample data
   e. wherein after the medical appliance is connected to the computer, setting up a data link between the medical appliance and the computer system using the communication protocol if the data received from the medical appliance correspond to the sample data.

11. A computer system for setting up a data link to appliances in which for each of the medical appliances at least one communication protocol is stored together with the communication parameters assigned to this communication protocol, the computer system:
   a. setting communication parameters of a communication protocol;
   b. receiving data from a medical appliance;
   c. checking whether the data received from the medical appliance corresponds to sample data which are characteristic for the communication protocol;
   d. repeating steps a. to c. with other communication parameters of the communication protocol if the data received from the medical appliance do not correspond to the sample data;
   e. setting up a data link between the medical appliance and the computer system using the communication protocol if the data received from the medical appliance correspond to the sample data.

12. The system according to claim 11, repeating steps a. to e with at least one further communication protocol if it was not possible to set up a data link between the medical appliance and the computer system.

13. The system according to claim 11, repeating steps a. to e. for at least one further medical appliance.

14. The system according to claim 11, assigning the communication parameters to a communication protocol occurring in this communication protocol with different likelihood and in step a. those communication parameters being set which have the highest likelihood.

15. The system according to claim 11, wherein the sample data characteristic for the respective communication protocol unambiguously differs from sample data of other communication protocols.

16. The system according to claim 11, wherein the sample data characteristic for a communication protocol is established by an analysis of response data from a medical appliance.

17. The system according to claim 11, before step b. a request is sent to the medical appliance and in step b. the data sent from the medical appliance upon the request made of the medical appliance being received by the computer system.

18. The system according to claim 11, wherein before setting up the data link in step e., the computer system examines whether the first communication protocol has been unambiguously identified.

19. The system according claim 11, wherein the computer system assigns and activates a software driver module in order to set up the data link in step e. to the medical appliance assigned to the communication protocol.

20. A computer system for determining a communication protocol between a computer and a medical appliance prior to connecting the appliance to a computer, the computer system:
  a. setting communication parameters of the communication protocol;
  b. deriving sample data by analyzing response data to be expected of the medical appliance according to manufacturer specifications;
  c. checking whether the derived sample data of the medical appliance corresponds to sample data which are characteristic for the communication protocol;
  d. repeating steps a. to c. with other communication parameters of the communication protocol if the derived sample data from the medical appliance do not correspond to the sample data;
  e. wherein after the medical appliance is connected to the computer, setting up a data link between the medical appliance and the computer system using the communication protocol if the data received from the medical appliance correspond to the sample data.

21. The method according claim 1, wherein the communication parameters are a data transmission rate, a number of data bits in a data word, parity bit, a number of stop bits, a number of start bits, and a flow control.

22. The system according claim 11, wherein the communication parameters are a data transmission rate, a number of data bits in a data word, parity bit, a number of stop bits, a number of start bits, and a flow control.

* * * * *